(12) United States Patent
Veasey et al.

(10) Patent No.: US 10,420,897 B2
(45) Date of Patent: Sep. 24, 2019

(54) SUPPLEMENTAL DEVICE FOR ATTACHMENT TO AN INJECTION DEVICE

(71) Applicant: SANOFI-AVENTIS DEUTSCHLAND GMBH, Frankfurt am Main (DE)

(72) Inventors: Robert Veasey, Warwickshire (GB); David Aubrey Plumptre, Worcestershire (GB); Paul Richard Draper, Worcestershire (GB); David Richard Mercer, Dorset (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 415 days.

(21) Appl. No.: 14/783,174

(22) PCT Filed: May 2, 2014

(86) PCT No.: PCT/EP2014/058969
§ 371 (c)(1),
(2) Date: Oct. 8, 2015

(87) PCT Pub. No.: WO2014/180744
PCT Pub. Date: Nov. 13, 2014

(65) Prior Publication Data
US 2016/0030680 A1 Feb. 4, 2016

(30) Foreign Application Priority Data
May 7, 2013 (EP) .................................... 13166723

(51) Int. Cl.
*A61M 5/315* (2006.01)
(52) U.S. Cl.
CPC ...... *A61M 5/31568* (2013.01); *A61M 5/3155* (2013.01); *A61M 2205/3327* (2013.01); *A61M 2205/505* (2013.01)

(58) Field of Classification Search
CPC ............ A61M 5/31568; A61M 5/3155; A61M 2205/3327; A61M 2205/505; A61M 5/24;
(Continued)

(56) References Cited

U.S. PATENT DOCUMENTS 533,575 A 2/1895 Wilkens
5,226,895 A 7/1993 Harris
(Continued)

FOREIGN PATENT DOCUMENTS

EP 0615762 9/1994
EP 0937471 8/1999
(Continued)

OTHER PUBLICATIONS

European Search Report for EP App. No. 13166723, completed Oct. 9, 2013.
(Continued)

*Primary Examiner* — Laura A Bouchelle
*Assistant Examiner* — Dung T Ulsh
(74) *Attorney, Agent, or Firm* — Fish & Richardson P.C.

(57) ABSTRACT

A supplemental device for attachment to an injection device, the supplemental device having a housing containing at least two electromechanical switches each having an open state and a closed state and a protrusion associated with each switch configured to protrude from the housing so as to contact a rotatable surface of the injection device while the supplemental device is attached to the injection device; and a processor arrangement configured to detect a change in the state of each of the switches; and to determine a direction of rotation of the rotatable surface of the injection device from the detected state changes.

11 Claims, 7 Drawing Sheets

(58) Field of Classification Search
CPC .......... A61M 5/31525; A61M 5/31535; A61M 5/3129; A61M 5/31533; A61M 5/31565; A61M 5/31566; A61M 5/31573; G06F 19/3468
See application file for complete search history.

(56) References Cited

U.S. PATENT DOCUMENTS

| | | | |
|---|---|---|---|
| 5,279,586 A * | 1/1994 | Balkwill | A61M 5/3158 222/309 |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,509,905 A | 4/1996 | Michel | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,278,677 B1 * | 8/2001 | Sako | G11B 17/225 720/607 |
| 6,899,698 B2 | 5/2005 | Sams | |
| 6,936,032 B1 | 8/2005 | Bush, Jr. et al. | |
| 7,241,278 B2 | 7/2007 | Moller | |
| 8,197,449 B2 * | 6/2012 | Nielsen | A61M 5/3155 604/187 |
| 9,649,448 B2 * | 5/2017 | Madsen | A61M 5/31568 |
| 2002/0052578 A1 | 5/2002 | Moller | |
| 2002/0120235 A1 | 8/2002 | Enggaard | |
| 2003/0050609 A1 | 3/2003 | Sams | |
| 2003/0130853 A1 | 7/2003 | Maire | |
| 2003/0187405 A1* | 10/2003 | Gatti | A61M 5/31553 604/207 |
| 2004/0059299 A1 | 3/2004 | Moller | |
| 2004/0186441 A1* | 9/2004 | Graf | A61M 5/315 604/207 |
| 2004/0210199 A1 | 10/2004 | Atterbury et al. | |
| 2004/0215153 A1* | 10/2004 | Graf | A61M 5/315 604/218 |
| 2004/0267207 A1 | 12/2004 | Veasey et al. | |
| 2005/0085776 A1* | 4/2005 | Hommann | A61M 5/31553 604/207 |
| 2005/0113765 A1 | 5/2005 | Veasey et al. | |
| 2005/0182360 A1 | 8/2005 | Yeandel et al. | |
| 2006/0153693 A1 | 7/2006 | Fiechter et al. | |
| 2006/0224123 A1 | 10/2006 | Friedli et al. | |
| 2008/0287865 A1* | 11/2008 | Nielsen | A61M 5/3155 604/65 |
| 2009/0012479 A1* | 1/2009 | Moller | A61M 5/20 604/211 |
| 2009/0275916 A1 | 11/2009 | Harms et al. | |
| 2014/0194825 A1* | 7/2014 | Nielsen | A61M 5/24 604/189 |
| 2014/0194829 A1* | 7/2014 | Baek | A61M 5/31551 604/207 |
| 2015/0297835 A1* | 10/2015 | Hoeholt | A61M 5/24 604/191 |

FOREIGN PATENT DOCUMENTS

| | | |
|---|---|---|
| EP | 0937476 | 8/1999 |
| JP | 2003-010327 | 1/2003 |
| WO | 99/38554 | 8/1999 |
| WO | 01/10484 | 2/2001 |
| WO | 2006/045523 | 5/2006 |
| WO | WO 2009/062675 | 5/2009 |
| WO | WO 2010/052275 | 5/2010 |
| WO | 2011/117212 | 9/2011 |
| WO | 2012/127046 | 9/2012 |
| WO | 2013/004844 | 1/2013 |

OTHER PUBLICATIONS

International Search Report and Written Opinion for Int. App. No. PCT/EP2014/058969, dated Jul. 7, 2014.
International Preliminary Report on Patentability in International Application No. PCT/EP2014/058969, dated Nov. 10, 2015, 6 pages.

* cited by examiner

SUPPLEMENTAL DEVICE FOR ATTACHMENT TO AN INJECTION DEVICE

CROSS REFERENCE TO RELATED APPLICATIONS

The present application is a U.S. National Phase Application pursuant to 35 U.S.C. § 371 of International Application No. PCT/EP2014/058969 filed May 2, 2014, which claims priority to European Patent Application No. 13166723.0 filed May 7, 2013. The entire disclosure contents of these applications are herewith incorporated by reference into the present application.

TECHNICAL FIELD

The present invention relates to a supplemental device for attachment to an injection device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen.

It has been described, for instance in WO 2011/117212 to provide a supplemental device comprising a mating unit for releasably attaching the device to an injection device. This device includes a camera and is configured to perform optical character recognition (OCR) on captured images visible through a dosage window of the injection pen, thereby to determine a dose of medicament that has been dialed into the injection device.

SUMMARY

A first aspect of the invention provides a supplemental device for attachment to an injection device, the supplemental device comprising:
 a housing containing at least two electromechanical switches each having an open state and a closed state and a protrusion associated with each switch configured to protrude from the housing so as to contact a rotatable surface of the injection device while the supplemental device is attached to the injection device; and
 a processor arrangement configured to:
 detect a change in the state of each of the switches; and
 determine a direction of rotation of the rotatable surface of the injection device from the detected state changes.
The housing may contain a first electromechanical switch and a second electromechanical switch and the actuators of the first and second electromechanical switches may be arranged so as to contact the rotatable surface of the injection device at different relative circumferential positions.

The rotatable surface may be corrugated and each switch may have a first state when its respective actuator is located in a trough of a corrugation and a second state when its respective actuator is located on a crest of a corrugation. The first state may be an open state and the second state may be a closed state.

The supplemental device may be configured such that, when it is attached to an injection device having a corrugated rotatable surface and when the rotatable surface is in a rotational position representing an integer dose value, the first and second switches both have either the first state or the second state. An increase or decrease of one integer dose unit in the rotational position of the rotatable surface may cause the state of the first and second switches to change from an initial state to the opposite state and back to the initial state. An increase or decrease of one integer dose unit in the rotational position of the rotatable surface may cause the state of the first and second switches to change from an initial state to the opposite state.

An increase or decrease of one integer dose unit in the rotational position of the rotatable surface may cause the state of one of the two switches to change from an initial state to the opposite state while the state of the other of the two switches does not change.

The supplemental device may be configured such that, when it is attached to an injection device having a corrugated rotatable surface and when the rotatable surface is in a rotational position representing an integer dose value, the first switch has the first state and the second switch has the second state. An increase or decrease of one integer dose unit in the rotational position of the rotatable surface may cause the state of the first and second switches to change from their respective initial states to the opposite states and back to their initial states. An increase or decrease of one integer dose unit in the rotational position of the rotatable surface may cause the state of the first and second switches to change from their respective initial states to the opposite states.

The processor arrangement may be configured to determine a direction of rotation of the rotatable surface from the order in which the states of the first and second switches change.

An increase or decrease of one integer dose unit in the rotational position of the rotatable surface may cause the state of one of the two switches to change from an initial state to the opposite state and back to the initial state and causes the state of the other of the two switches to change from an initial state to the opposite state.

A second aspect of the invention provides a system comprising the supplemental device of the first aspect of the invention and an injection device having a corrugated rotatable surface configured to rotate when a dose is dialed into or out of the injection device.

The rotatable surface may be a cylindrical surface and a 360 degree rotation of the cylindrical surface may correspond to 24 integer dose units.

BRIEF DESCRIPTION OF THE FIGURES

Embodiments will now be described, by way of example only, with reference to the accompanying drawings, in which.

DETAILED DESCRIPTION

In the following, embodiments of the present invention will be described with reference to an insulin injection device. The present invention is however not limited to such application and may equally well be deployed with injection devices that eject other medicaments, or with other types of medical devices.

Figure 1:
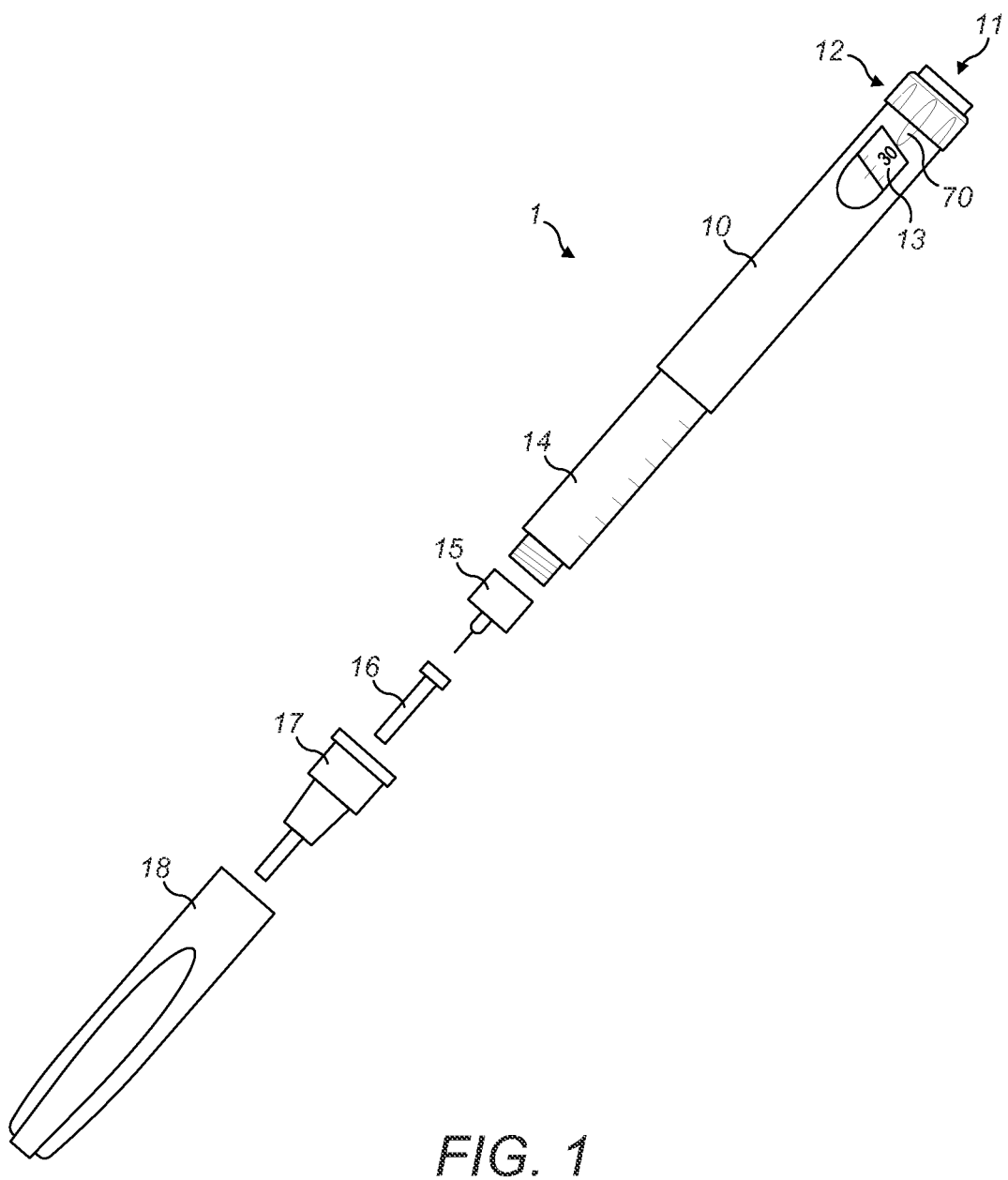
FIG. 1 is an exploded view of an injection device.

FIG. 1 is an exploded view of an injection device 1, which may for instance represent Sanofi's Solostar (R) insulin injection pen, or Sanofi's Quadrant insulin injection pen.

The injection device 1 of FIG. 1 is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning (or "dialing") the dosage knob 12, and the selected dose is then displayed via dosage window 13, for instance in multiples of so-called International Units (IU), also referred to herein as dose units. One IU is the biological equivalent of about 45.5 micrograms of pure crystalline insulin (1/22 mg). An example of a selected dose displayed in dosage window 13 may for instance be 30 IUs, as shown in FIG. 1. It should be noted that the selected dose may equally well be displayed differently, for instance by means of an electronic display.

Turning the dosage knob 12 may cause a mechanical click sound to provide acoustical feedback to a user. The numbers displayed in dosage window 13 are printed on a sleeve that is contained in housing 10 and mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached. Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

Figure 2:
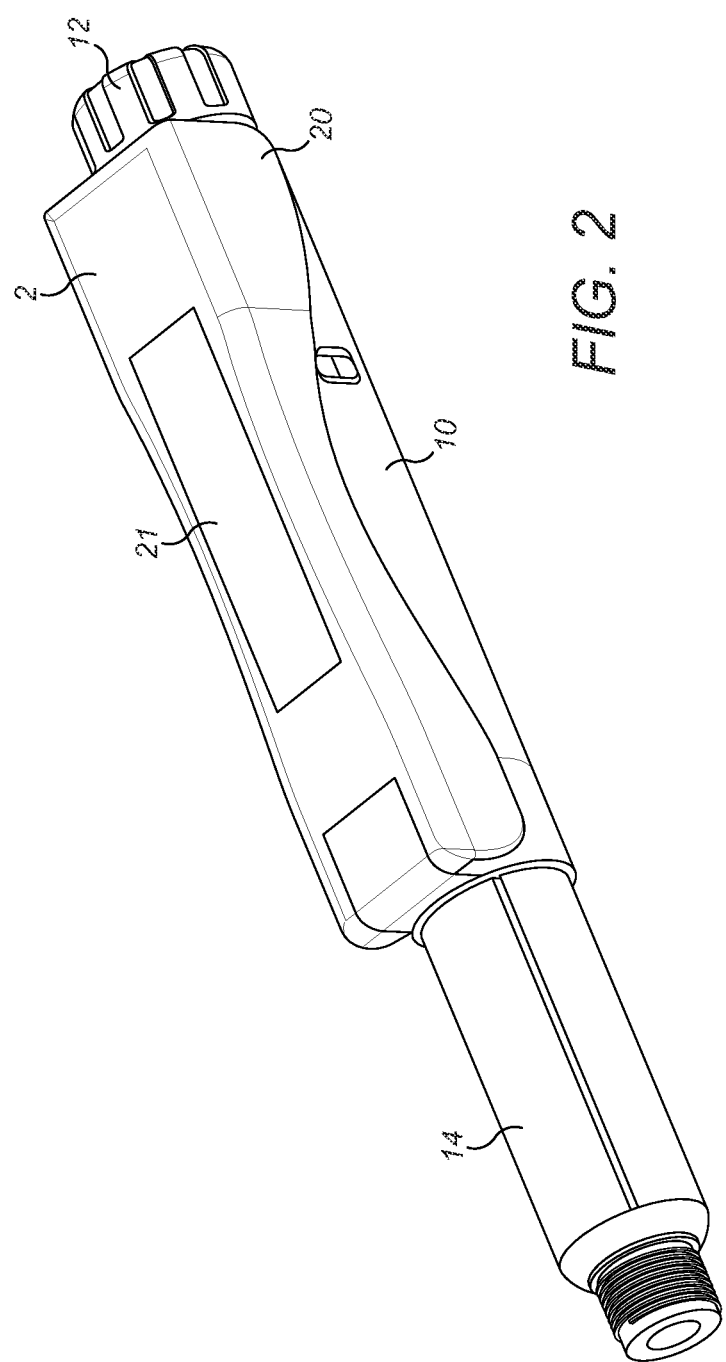
FIG. 2 is a perspective view of the injection device of FIG. 1 with a supplemental device according to embodiments of the invention attached.

FIG. 2 shows an embodiment of a supplemental device 2 attached to injection device 1 of FIG. 1. The supplemental device 2 comprises a housing 20 with a mating unit configured and embrace the housing 10 of the injection device 1 of FIG. 1, so that the supplemental device 2 sits tightly on the housing 10, but is nevertheless removable from the injection device 1, for instance when the injection device 1 is empty and has to be replaced. The supplemental device 2 may be elongate, as shown in FIG. 2, extending over substantially the whole of the housing 10 of the injection device 1. Alternatively, the supplemental device 2 may be shorter, covering only a portion of the housing 10. The supplemental device 2 may have any suitable shape.

The supplemental device 2 may have a display unit 21. Information, such as dosage readings, dosage history, instructions, warnings or supplemental device settings may be displayed via the display unit 21. The supplemental device 2 may also have one or more user inputs (not shown). These may comprise buttons or touch sensitive regions on the housing 20 of the device 2. These user inputs may allow a user to turn on/off the supplemental device 2, to trigger actions (for instance to cause establishment of a connection to or a pairing with another device, and/or to trigger transmission of information from supplemental device 2 to another device), or to confirm something.

The supplemental device 2 also comprises a processor arrangement (not visible) and a memory (not visible) for storing program instructions. The program and processor arrangement together control operation of the supplemental device 2, including receiving and interpreting signals from switches (described in greater detail below) housed within the device.

Figure 3:
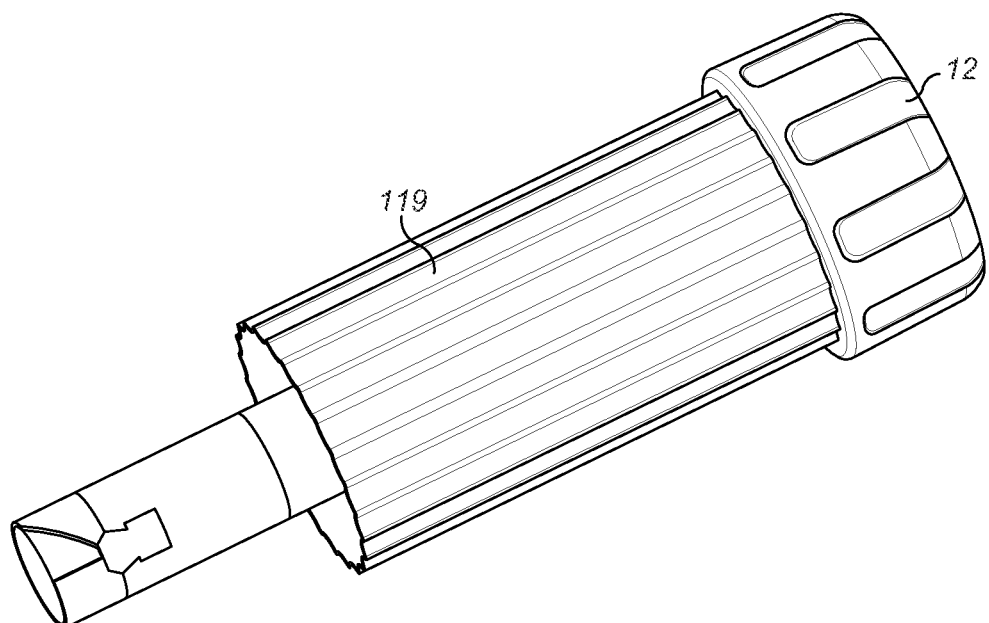
FIG. 3 is a perspective view of a dialing sleeve component of the injection device of FIG. 1.
Figure 4:
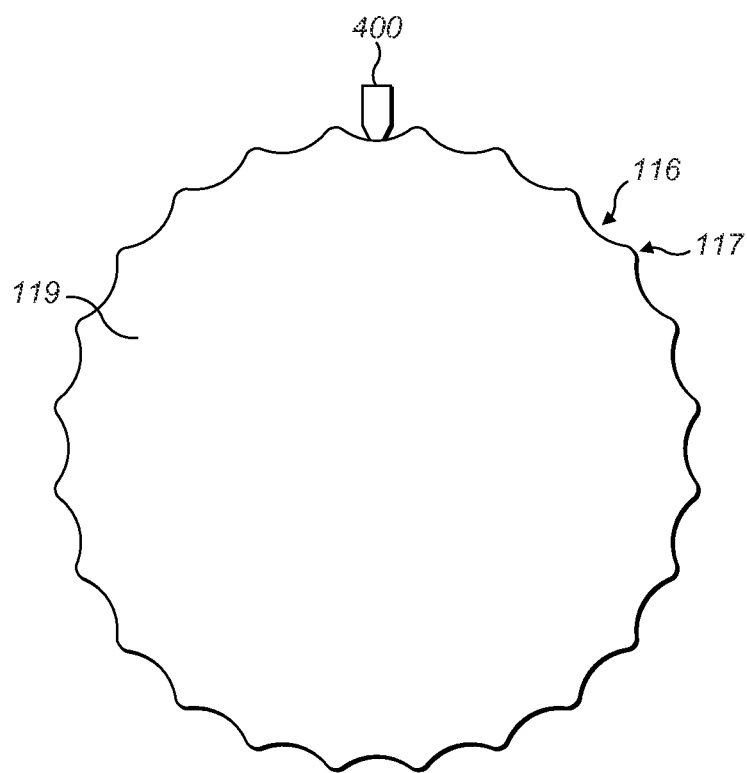
FIG. 4 is a cross-sectional view of the dialing sleeve component of FIG. 3 also showing a switch actuator.

Referring now to FIGS. 3 and 4, the injection device 1 to which the supplemental device 2 is to be attached has a corrugated dialing sleeve 119. The corrugations (which may also be referred to as splines, undulations or ridges) are defined by troughs 116 and crests 117. The dialing sleeve 119 is configured to rotate with the dosage knob 12 during dose dialing. The dialing sleeve 119 may be coupled directly to or be integral with the dosage knob 12. As a dose is dialed into the injection device (dialing up), the dialing sleeve 119 rotates and extends axially outwards from the housing 10. As a dose is dialed out of the injection device (dialing down), the dialing sleeve 119 rotates in the opposite direction and moves back into the housing 10.

The supplemental device 2 may house an electromechanical switch arrangement (not shown). The electromechanical switch arrangement may comprise a self-contained unit which is fitted to the supplemental device 2. The electromechanical switch arrangement may for example be housed in a recess in the underside of the supplemental device 2 (the part which contacts the injection device 1). The electromechanical switch arrangement may be secured to the supplemental device 2 by friction or by an interlocking arrangement (not shown), or alternatively by screws, adhesive or the like. In some alternative embodiments, the electromechanical switch arrangement is an integral part of the housing 20 of the supplemental device 2. A lower part of the electromechanical switch arrangement is concave in shape and matches the curvature of the injection device 1. The lower part of the electromechanical switch arrangement abuts several of the crests 117 of the corrugated dialing sleeve 119 but the dialing sleeve 119 is free to rotate relative to supplemental device 2. The lower part of the electromechanical switch arrangement may have one or more apertures.

At least two switches are mounted inside the electromechanical switch arrangement. Each switch may be an electromechanical micro switch of any suitable type. Each switch has an actuator 400 (also referred to herein as a protrusion, member or limb) and is arranged such that the free end of the actuator passes through an aperture in the electromechanical switch arrangement and protrudes from the housing 20 of the supplemental device 2. An internal spring may bias each switch actuator 400 towards a protruding position, in which the switch actuator abuts and is forced against the surface of the dialing sleeve 119 when the supplemental device 2 is attached, as illustrated in FIG. 4. The skilled person will be aware of various constructions suitable for the electromechanical switches. For example, the switch actuators 400 may be protrusions coupled to an internal member. The internal member may be rotatably mounted. Switch contacts may be disposed on the internal member, or a protruding limb of the internal member. Alternatively, the protrusion which contacts the dialing sleeve surface may also comprise switch contacts on an internal surface such that no intermediary switching members are required.

In some embodiments, the injection device 1 is configured such that a small portion of the dialing sleeve 119 adjacent the dosage button 12 extends out of the housing 10 of the injection device 1 when no dose has been dialed. This allows the switch actuators 400 to contact the dialing sleeve 119 at all times during operation of the device.

Each switch may have electrical contacts supported on an internal surface. These contacts are arranged to be engaged by corresponding electrical contacts on an internal part of each switch actuator 400. The skilled person will be aware of other contact arrangements which may be used as the exact internal structure of the switches is not limiting on the scope of the invention. In any case, the contacts are arranged such that the state of the switch (open or closed) depends on whether the switch actuator 400 is located in a trough 116 or on a crest 117 of the dialing sleeve 119. The supplemental device 2 comprises a processor arrangement. The processor arrangement is configured to control the application of signals to the contacts and to detect when each switch is open or closed.

In some embodiments of the invention, the electromechanical switch arrangement comprises two switches, each switch having an actuator. The two switch actuators are arranged to be spaced circumferentially relative to the dialing sleeve 119 such that each actuator contact the dialing sleeve at a different angular position. The switch actuators may be arranged to be at the same or different longitudinal positions relative to the dialing sleeve. Alternatively, the supplemental device 2 may comprise two separate electromechanical switch arrangements, each comprising a switch and being retained by different part of the supplemental device 2 such that the actuators of the respective switches are spaced circumferentially relative to the dialing sleeve 119. Further description of these embodiments will now be given with reference to FIGS. 5 to 8.

When a user wishes to dial in a dose to the injection device 1, the user grips the dosage knob 12 and rotates it. In some examples of the injection device 1, one full rotation (360 degrees) of the dialing sleeve corresponds to 24 medicament units. The mechanism internal to the injection device 1 is such that only integer units may be dialed into the device. Biasing means internal to the injection device ensure that the dialing sleeve 119 is at equilibrium only when an integer number of dose units are dialed in.

Figure 5A:
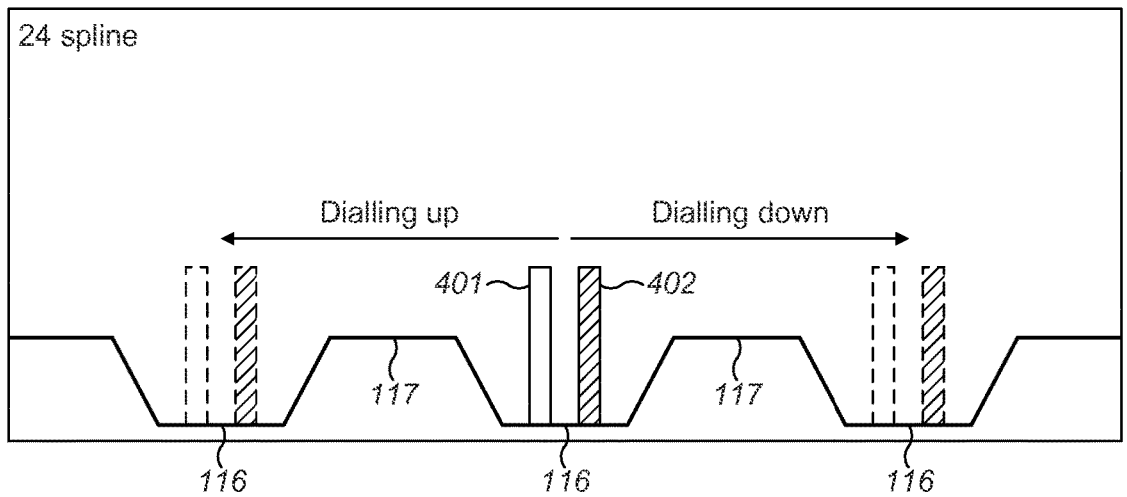
FIG. 5a is a schematic diagram showing the positions of switch actuators in contact with the dialing sleeve component in a first embodiment of the invention.
Figure 5B:
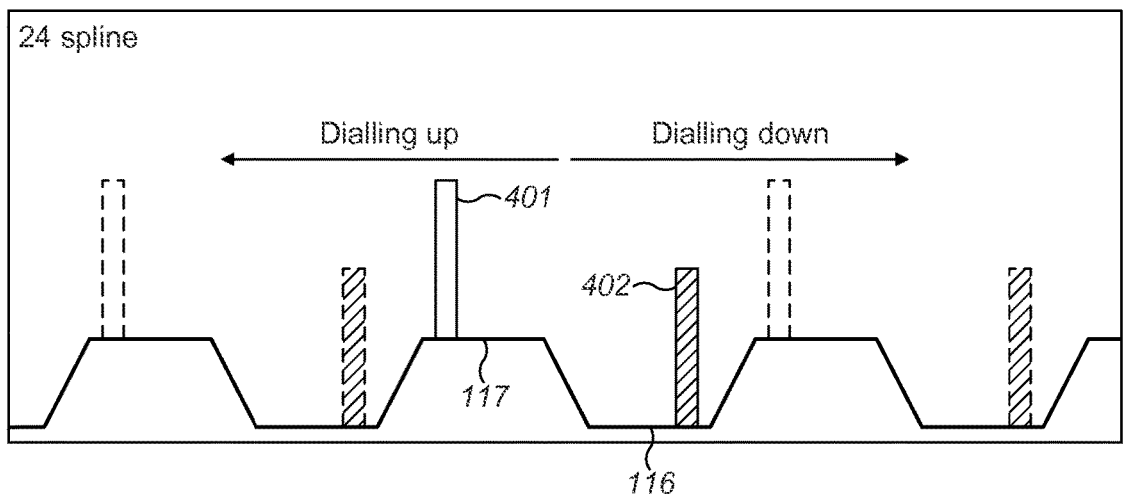
FIG. 5b is a schematic diagram showing the positions of switch actuators in contact with the dialing sleeve component in a second embodiment of the invention.

In some embodiments the dialing sleeve 119 comprises 24 corrugations. In other words the dialing sleeve 119 has 24 troughs 116 and 24 crests 117. Referring now to FIGS. 5a and 5b, two embodiments are shown in which the dialing sleeve 119 comprises 24 corrugations. FIG. 5a shows a first switch actuator 401 comprising part of the first electromechanical switch and a second switch actuator 402 comprising a part of the second electromechanical switch. This figure also illustrates the first switch actuator dialed up position and dialed down position indicated by the rectangles having a dashed outer boundary and no fill, and the second switch actuator dialed up position and dialed down position indicated by the rectangles having a dashed outer boundary and hashed filling. The positions of the first switch actuator 401 and second switch actuator 402 shown using a solid outer boundary may indicate an initial position of the two switch actuators 401 and 402. The switch actuator positions shown to the left of this initial position illustrate the positional change occurring when one integer dose unit is dialed into the injection device 1. The switch actuator positions shown to the right of this initial position illustrate the positional change occurring when one integer dose unit is dialed out of the injection device 1.

In the embodiment of FIG. 5a, both switch actuators 401, 402 are located in a trough 116 of a corrugation in the initial position and after one dose unit has been dialed in or dialed out. For example, starting from the initial position, when one dose unit is dialed in, the switch actuators 401, 402 move left relative to the surface of the dialing sleeve 119. The first switch actuator 401 is the first to ascend the incline to the left, followed by the second switch actuator 402. When the switch actuators 401, 402 reach the top of a crest 117, the state of their respective electromechanical switches changes. For example, the switches may have an open state when their respective switch actuator is located in a trough 116 and a closed state when their respective actuator is located on a crest 117, or vice versa. The switch actuators 401, 402 continue to move to the left until they reach the adjacent trough 116. At this point one integer unit of medicament has been dialed into the injection device 1. In this embodiment, both switch actuators 401, 402 may equally be located on a crest 117 of a corrugation in the initial position and after one dose unit has been dialed in or dialed out.

As can be seen in FIGS. 5 to 8 the troughs 116 and crest 117 of the corrugations may be flat areas linked by straight inclines. However in some other embodiments the troughs 116 may comprise a flat area while the crest 117 may comprise a smooth curve linking adjacent troughs as shown in FIG. 4. Alternatively the corrugation may comprise a smooth undulation, such as a sine wave.

Referring now to FIG. 5b a second embodiment is shown in which the dialing sleeve 119 comprises 24 corrugations. In this embodiment the relative separation of the first and second switch actuators 401, 402 is greater than in the embodiment of FIG. 5a. The separation of the switch actuators 401, 402 is such that when the dialing sleeve 119 is located in an integer dose unit position, the first and second electromechanical switches have different states. Exemplary initial positions of the first and second switch actuators 401, 402 are illustrated by the rectangles having solid outer boundaries. The positions of the first and second switch actuators after one dose unit has been dialed in or dialed out are illustrated by the rectangles having dashed outer boundaries. In this embodiment the first switch actuator 401 is located on a crest 117 while the second switch actuator 402 is initially located in a trough 116 in every integer unit dose position. Thus the first electromechanical switch may have a closed state while the second electromechanical switch has an open state. When a dose unit is dialed into the injection device 1 the first electromechanical switch is opened before the second electromechanical switch is closed. When a dose unit is dialed out of the injection device 1 the second electromechanical switch is closed before the first electromechanical switch is opened. This occurs because the first switch actuator 401 is located close to a boundary between a crest 117 and a trough 116 in a first direction (the dialing up direction), but not on the other while the second switch actuator 402 is located close to a boundary between a crest 117 and a trough 116 in a second direction (the dialing down direction), but not on the other. Thus the processor of the supplemental device 2 is able to determine the direction of rotation of the dialing sleeve 119 by monitoring the signals received from the first and second electromechanical switches.

In the embodiments of FIGS. 5a and 5b, the dialing in or out of one unit dose causes both the first and second electromechanical switches to change from their initial state to the opposite state and back again. The processor may use this series of state changes to determine incrementally the number of units which have been dialed into or out of the injection device 1.

Figure 6A:
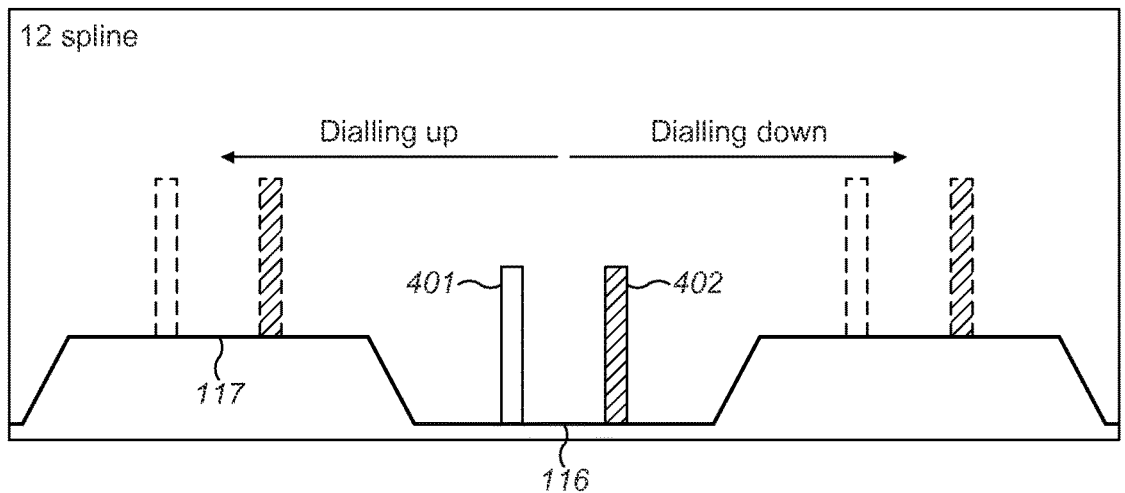
FIG. 6a is a schematic diagram showing the positions of switch actuators in contact with the dialing sleeve component in a third embodiment of the invention.
Figure 6B:
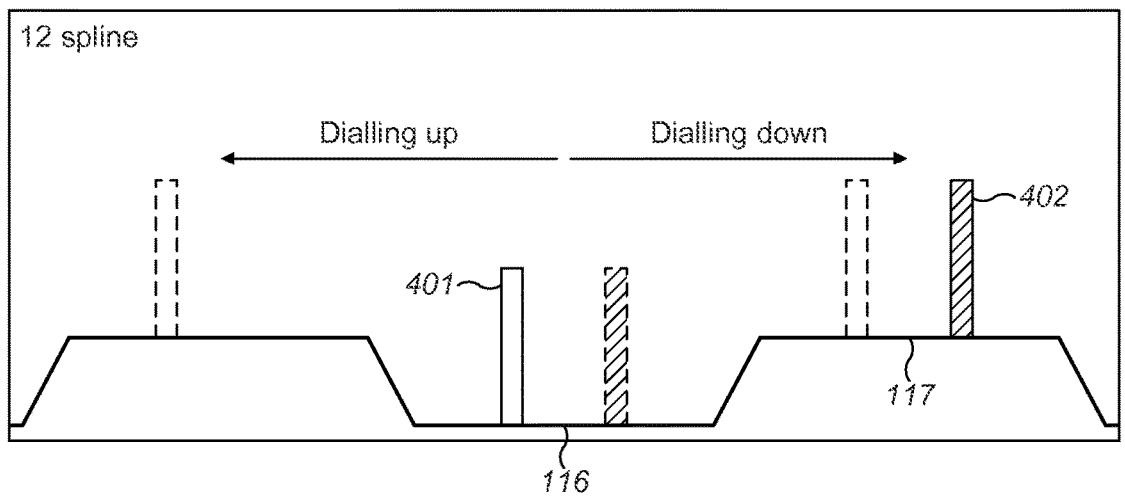
FIG. 6b is a schematic diagram showing the positions of switch actuators in contact with the dialing sleeve component in a fourth embodiment of the invention.

Referring now to FIGS. 6a and 6b, two embodiments are shown in which the dialing sleeve 119 comprises 12 corrugations. It may be advantageous to reduce the number of corrugations of the dialing sleeve 119 in order to reduce the effect of manufacturing tolerances of the dialing sleeve 119 and of the electromechanical switches on the reliability of the switches. Reducing the number of corrugations may also make the dialing sleeve 119 easier and more cost effective to produce. In the embodiment of FIG. 6a both the first and second switch actuators 401 and 402 are located in a trough 116 of a corrugation, however they may equally both be located on a crest 117 of a corrugation. When one unit is dialed into the injection device 1, both the first and second switches change state once, for example from an open state to a closed state. The processor may determine the direction of rotation of the dialing sleeve 119 in the same way as for the embodiment of FIG. 5a, i.e. the first electromechanical switch changes state before the second electromechanical switch when a dose unit is dialed in and the second electromechanical switch changes state before the first electromechanical switch when a dose unit is dialed out.

In the embodiments shown in FIG. 6b the switch actuators are separated by a greater distance than in the embodiment of FIG. 6a such that initially the first switch actuator 401 is located in a trough while the second switch actuator 402 is located on a crest. FIG. 6b also shows the position of the first and second switch actuators 401 and 402 after one unit has been dialed into the device. In this position the states of the first and second electromechanical switches have been reversed. The position of the first switch actuator 401 after one unit has been dialed out of the device can also be seen. The position of the second switch actuator 402 after one unit has been dialed out is not visible. Similarly to the embodiment shown in FIG. 5b, the separation between the first and second switch actuators is greater than the distance between the centre point of adjacent troughs 116 and crests 117. Thus when a dose is dialed into or out of the device, one of the switches changes state before the other allowing the processor to determine the direction of rotation of the dialing sleeve 119. Having 12 corrugations as opposed to 24 corrugations increases the length of the troughs 116 and crests 117. This increases the margin for error in the separation of the first and second switch actuators 401, 402 which in turn increases the reliability of the system.

Figure 7:
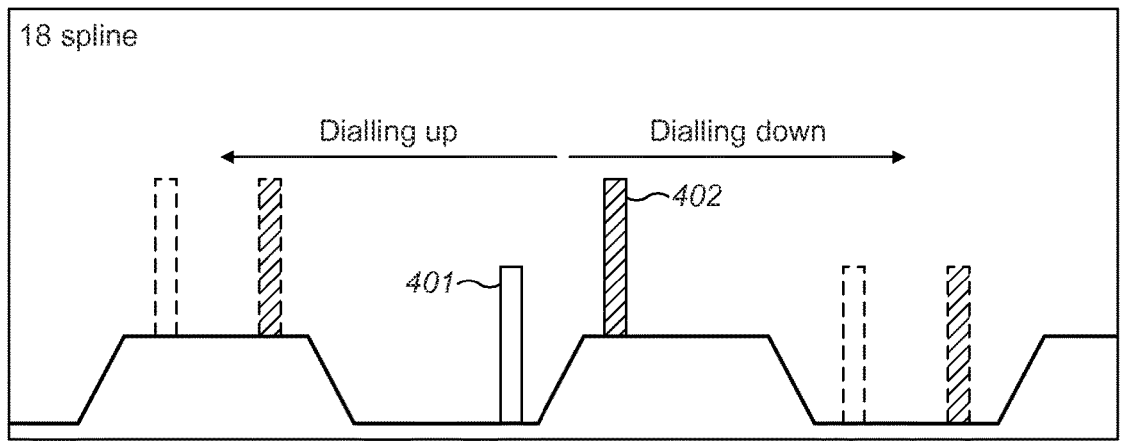
FIG. 7 is a schematic diagram showing the positions of switch actuators in contact with the dialing sleeve component in a fifth embodiment of the invention.

FIG. 7 illustrates an embodiment in which the dialing sleeve 119 comprises 18 corrugations. The separation of the switch actuation members 401, 402 is chosen such that when one unit is dialed in or out of the device, one of the switches changes state once while the other switch changes state twice. For example, if the initial positions of the switch actuators 401, 402 are as shown in FIG. 7, with the first switch actuator 401 located in a trough 116 the second switch actuator 402 located on a crest 117, when one unit is dialed into the device the first switch changes from an open state to a closed state while the second switch changes from a closed state to an open state and then back to a closed state. If one unit is dialed out of the device from the initial position, the second switch changes from a closed state to an open state while the first switch changes from an open state to a closed state and back again.

In the embodiments shown in FIGS. 5a to 6b, the processor must monitor the order in which the first and second switches change state in order to determine the direction of rotation of the dialing sleeve 119. In the embodiment of FIG. 7, the processor does not need to monitor the order in which the switch state changes occur since each of the first and second electromechanical switches changes state once or twice for each dose unit dialed depending on the direction of rotation. In the embodiments of FIG. 7 the first and second electromechanical switches, when taken together, may represent any one of four states. These are: both switches closed, first switch open and second switch closed, both switches open and first switch closed and second switch open. As will be appreciated from FIG. 7, the order in which these states occur depends on the direction of rotation of the corrugated dialing sleeve. Thus the processor need only know the states of the switches at each integer dose unit position in order to determine a direction of rotation. This may have the advantage of reducing the complexity and power requirements of the processor as the processor does not have to monitor continuously the state changes of the switches.

Figure 8:
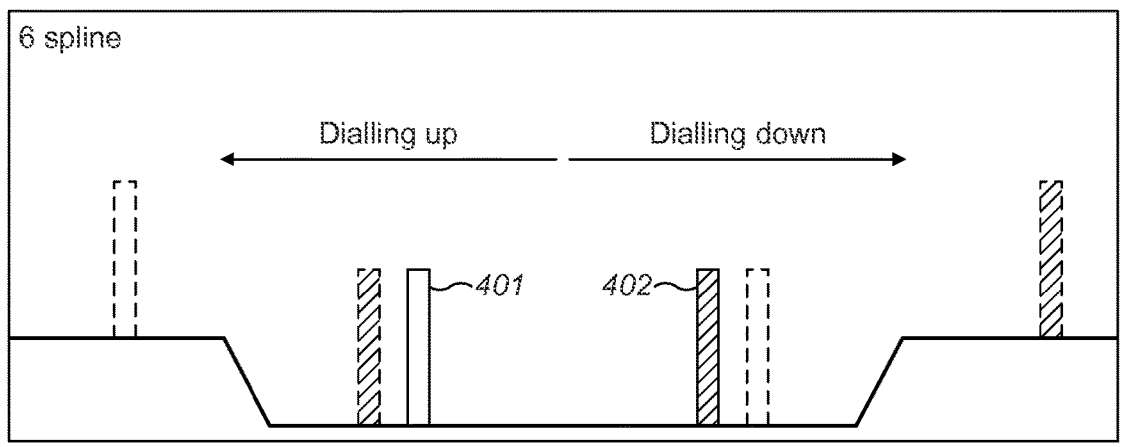
FIG. 8 is a schematic diagram showing the positions of switch actuators in contact with the dialing sleeve component in a sixth embodiment.

FIG. 8 illustrates another embodiment in which the dialing sleeve 119 comprises only 6 corrugations. Similarly to the embodiment of FIG. 7, the first and second switch actuators 401, 402 are arranged such that, taken together, they define four different states. When one dose unit is dialed into or out of the device, one of the switches changes state once while the other switch remains in the same state. For example, given the initial positions of the first and second switch actuators shown in FIG. 8, when one unit is dialed into the device the first switch changes from an open state to a closed state while the second switch begins and ends in an open state. If a second unit is dialed into the device the first switch begins and ends in a closed state while the second switch changes from an open state to a closed state. As with the embodiment of FIG. 7, the processor does not need to monitor the order in which the first and second switches change state in order to determine the direction of rotation.

The processor only needs to know the start and end states of each of the switches to determine the direction.

With all of the embodiments described above, as the direction of rotation of the dialing sleeve can be determined the processor is also able to incrementally calculate the number of dose units dialed into the injection device 1. Provided that the supplemental device 2 is attached to the injection device 1 and activated when zero dose units are dialed in, this encoding method may be used to indicate the currently dialed dose to a user. For example the supplemental device, when attached to the injection device 1, may obscure the display window 13. Thus the processor may determine incrementally a dose dialed into the injection device 1 and display the dialed dose on the display unit 21 of the supplemental device 2. Alternatively or in addition, the supplemental device 2 may comprise an optical character recognition (OCR) system configured to read the dialed dose through the display window 13 and to display the result of this reading on the display unit 21. In some other embodiments the supplemental device 2 does not obscure the display window 13 when attached to the injection device 1. For example the display window 13 may be located further down the housing 10 of the injection device 1.

In some other embodiments, three or more electromechanical switches may be housed in the supplemental device 2, each having a switch actuator contacting the dialing sleeve 119. Although only two switches are required to determine a direction of rotation of the dialing sleeve 119, with more than two switches it is possible to achieve a quasi-absolute encoding of the dialing sleeve position and hence the currently dialed dose.

It will be appreciated that the above described embodiments are purely illustrative and not limiting on the scope of the claims. Other variations and modifications will be apparent to a person skilled in the art upon reading the application. For example, the electromechanical switches may be replaced by optical, magnetic, resistive or capacitive sensors.

For example, instead of corrugations the dialing sleeve 119 may have optical features, such as black and white regions, which can be detected by optical sensors or conductive and non-conductive regions which may be detected by magnetic, resistive or capacitive sensors.

For example, each electromechanical switch may be replaced by a camera. LEDs may also be present to aid in optical recognition. The corrugations may be replaced by parallel black lines having the same separation as adjacent crests of the corrugation.

In another exemplary alternative, the electromechanical switches may be replaced by contacts which protrude from the housing 20 of the supplemental device 2. These contacts may be configured to engage with conductive and non-conductive regions on the surface of the dialing sleeve 119.

In a further example, the electromechanical switches may be part of an injection device instead of a supplemental device. In a preferred embodiment of this example the corrugated surface is an inner surface. This improves handling as the overall device design is more compact. In addition having an inner corrugated surface leaves the outer surface smooth. Hence, when the outer surface is exposed it can be sealed against moisture and/or dust. Having the inner surface corrugated increases reliability because there is reduced ingression of dust and/or moisture and thus less impact on functionality.

Figure 9:
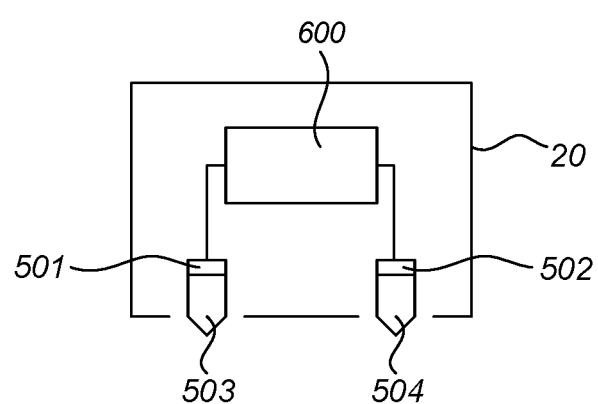
FIG. 9 is a schematic diagram showing first and second electromechanical switches protruding from a housing of the supplemental device.

As shown in FIG. 9 the supplemental device comprises a housing 20 containing a first electromechanical switch 501 and a second electromechanical switch 502, each switch having an open state and a closed state and an associated actuator 503 and 504. The actuators 503 and 504 associated with each switch 501 and 502 are arranged to protrude from the housing 20 so as to contact a rotatable surface of the injection device at different relative circumferential positions while the supplemental device is attached to the injection device.

The rotatable surface of the injection device is corrugated and each switch has a first state when its respective actuator is located in a trough of a corrugation and a second state when its respective actuator is located on a crest of a corrugation.

The supplemental device also comprises a processor arrangement 600 configured to detect a change in the state of each of the switches 501 and 502 and determine a direction of rotation of the rotatable surface of the injection device from the detected state changes.

Moreover, the disclosure of the present application should be understood to include any novel features or any novel combination of features either explicitly or implicitly disclosed herein or any generalisation thereof and during the prosecution of the present application or of any application derived therefrom, new claims may be formulated to cover any such features or combination of such features.

The invention claimed is:

1. A system comprising a supplemental device and an injection device, the supplemental device comprising:
    a housing containing a first electromechanical switch and a second electromechanical switch, each electromechanical switch having an open state and a closed state and an associated actuator, wherein the actuators associated with each electromechanical switch are arranged to protrude from the housing so as to contact a rotatable surface of a dialing sleeve of the injection device at different relative circumferential positions while the supplemental device is attached to the injection device; and
    a processor arrangement configured to:
        detect a change in the state of each of the electromechanical switches; and
        determine a direction of rotation of the rotatable surface of the injection device from the detected state changes,
    wherein the rotatable surface of the dialing sleeve is corrugated and is arranged to move rotationally and axially with respect to the housing, wherein each electromechanical switch has a first state when its respective actuator is located in a trough of a corrugation and a second state when its respective actuator is located on a crest of a corrugation, wherein the actuators are arranged to contact the rotatable surface during rotational and axial movement of the rotatable surface, wherein the rotatable surface is configured to rotate when a dose is dialed into or out of the injection device.

2. The system according to claim 1, wherein the rotatable surface is a cylindrical surface and wherein a 360 degree rotation of the cylindrical surface corresponds to 24 integer dose units.

3. The system according to claim 1, wherein the corrugated rotatable surface has a total of 24 individual corrugations.

4. The system according to claim 1, wherein the corrugated rotatable surface is arranged to move axially with respect to the housing when a dose is dialed into or out of the injection device.

5. The system according to claim 1, wherein the corrugated rotatable surface is coupled directly to, or is integral with, a dosage knob.

6. The system according to claim 1, wherein the corrugated rotatable surface is coupled directly to, or is integral with, a dosage knob.

7. The system according to claim 1, wherein the first state is an open state and the second state is a closed state.

8. The system according to claim 1, wherein the supplemental device configured such that, when it is attached to the injection device and when the rotatable surface is in a rotational position representing an integer dose value, the first electromechanical switch has the first state and the second electromechanical switch has the second state.

9. The system according to claim 8, wherein an increase or decrease of one integer dose unit in the rotational position of the rotatable surface causes the state of the first and second electromechanical switches to change from an initial state to an opposite state and back to the initial state.

10. The system according to claim 8, wherein an increase or decrease of one integer dose unit in the rotational position of the rotatable surface causes the state of the first and second electromechanical switches to change from an initial state to an opposite state.

11. The system according to claim 8, wherein an increase or decrease of one integer dose unit in the rotational position of the rotatable surface causes the state of one of the two electromechanical switches to change from an initial state to an opposite state and back to the initial state and causes the state of the other of the two electromechanical switches to change from an initial state to an opposite state.

\* \* \* \* \*